United States Patent [19]

Kumagai et al.

[11] Patent Number: 5,320,936

[45] Date of Patent: Jun. 14, 1994

[54] PHOTO RESPONSIVE MATERIAL EMPLOYING A THIOPHENE DERIVATIVE HAVING LONG CONJUGATED CHAIN AT 3-POSITIION

[75] Inventors: Hiroaki Kumagai, Tokyo; Tomokazu Iyoda, Hirakata; Takeo Shimizu, Uji, all of Japan

[73] Assignee: Canon Kabushiki Kaisha, Tokyo, Japan

[21] Appl. No.: 79,399

[22] Filed: Jun. 21, 1993

Related U.S. Application Data

[62] Division of Ser. No. 722,181, Jun. 27, 1991, Pat. No. 5,247,098.

[30] Foreign Application Priority Data

Jun. 27, 1990 [JP] Japan ................................. 2-166810

[51] Int. Cl.$^5$ .............................................. G03C 1/73
[52] U.S. Cl. ...................................... 430/495; 430/342; 430/343; 430/945; 430/962; 430/19; 252/586; 204/157.15
[58] Field of Search ............... 430/495, 342, 343, 962, 430/945, 19; 252/586; 204/157.15

[56] References Cited

U.S. PATENT DOCUMENTS

| | | | |
|---|---|---|---|
| 4,220,708 | 9/1980 | Heller | 430/336 |
| 4,766,198 | 8/1988 | Harper et al. | 528/377 |
| 4,992,347 | 2/1991 | Hawkins et al. | 430/10 |
| 5,183,726 | 2/1993 | Taniguchi et al. | 430/342 |

FOREIGN PATENT DOCUMENTS

| | | | |
|---|---|---|---|
| 51-075434 | 6/1976 | Japan | 430/342 |
| 63-172271 | 7/1988 | Japan | 430/495 |

OTHER PUBLICATIONS

Norval et al., Photochemistry and Photobiology, vol. 49, No. 5, pp. 633–639, "Urocanic Acid Analogs ... " (1989).

Trippett et al., "The use, in Wittig Reactions ... A basic Group" J. Chem. Soc., vol. 1266, pp. 2130–2133 (1961).

Archer et al., "Electrophilic Aromatic Substitution ... benzene" J. Chem. Soc., Perkin Trans. II, pp. 813–819 (1983) [Paper 2/13351].

*Primary Examiner*—Charles L. Bowers, Jr.
*Assistant Examiner*—John A. McPherson
*Attorney, Agent, or Firm*—Fitzpatrick, Cella, Harper & Scinto

[57] ABSTRACT

Thiophene derivatives represented by the general formula (I):

$$\underset{S}{\text{thiophene}}-(CH=CH)_n-R \quad (I)$$

where R is an aldehyde, carboxyl, $C_{1-5}$-alkyl ester or $C_{1-5}$-alkyl acetal group and n is 3 to 5, are prepared. These compounds are reversibly converted to their respective isomers by light irradiation, accompanied with a large shift of absorption and emission bands, thus suitable for a photo-responsive material.

17 Claims, 11 Drawing Sheets

FIG. I

PHOTO RESPONSIVE MATERIAL EMPLOYING A THIOPHENE DERIVATIVE HAVING LONG CONJUGATED CHAIN AT 3-POSITIION

This application is a division of application Ser. No. 07/722,181 filed Jun. 27, 1991, now U.S. Pat. No. 5,247,098.

BACKGROUND OF THE INVENTION

1. Field of the Invention

The present invention relates to a thiophene derivative having a long conjugated chain at the 3-position thereof, and to a material capable of responding to light (hereinafter referred to as photo-responsive material) employing the thiophene derivative. More particularly, the present invention relates to a thiophene derivative which has a long conjugated chain at the 3-position and isomerizes, by light irradiation, reversibly to only one other isomer having light-absorption bands and light-emission bands greatly different from those of the original isomer, and a photo-responsive material employing the thiophene derivative.

2. Related Background Art

Heretofore photo-responsive materials utilizing isomerization caused by light irradiation are known, including vitamin A (or retinal) derivatives, carotene derivatives, azo dye derivatives, and the like.

Among the above photo-responsive materials, vitamin A derivatives and carotene derivatives are disadvantageous in that four or more isomers are formed on light irradiation, and azo dye derivatives are disadvantageous in that the absorption wavelength changes caused by isomerization on light irradiation are small, which makes identification of the respective isomers difficult.

SUMMARY OF THE INVENTION

The present invention intends to provide a thiophene derivative having a long conjugated chain at the 3-position, reversibly convertible to only one isomer on light irradiation resulting in large changes in light-absorption bands end in light-emission bands between the isomers to allow ready identification of isomers and a photo-responsive material comprising the derivative which is applicable to an optical recording medium, an optical detecting material, and the like.

The present invention provides a thiophene derivative having a long conjugated chain at the 3-position thereof, represented by the general formula (I):

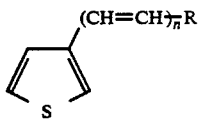
(I)

where R is a group selected from an aldehyde group, a carboxyl group, an alkyl ester group, and an alkyl acetal group, and n is an integer of from 3 to 5.

The present invention also provides a photo-responsive material containing a thiophene derivative having a long conjugated chain at the 3-position thereof, represented by the general formula (I) above.

The present invention further provides a method for isomerizing, by light-irradiation, a thiophene derivative having a long conjugated chain at the 3-position thereof, represented by the general formula (I) above.

DESCRIPTION OF THE PREFERRED EMBODIMENT

Figure 1:
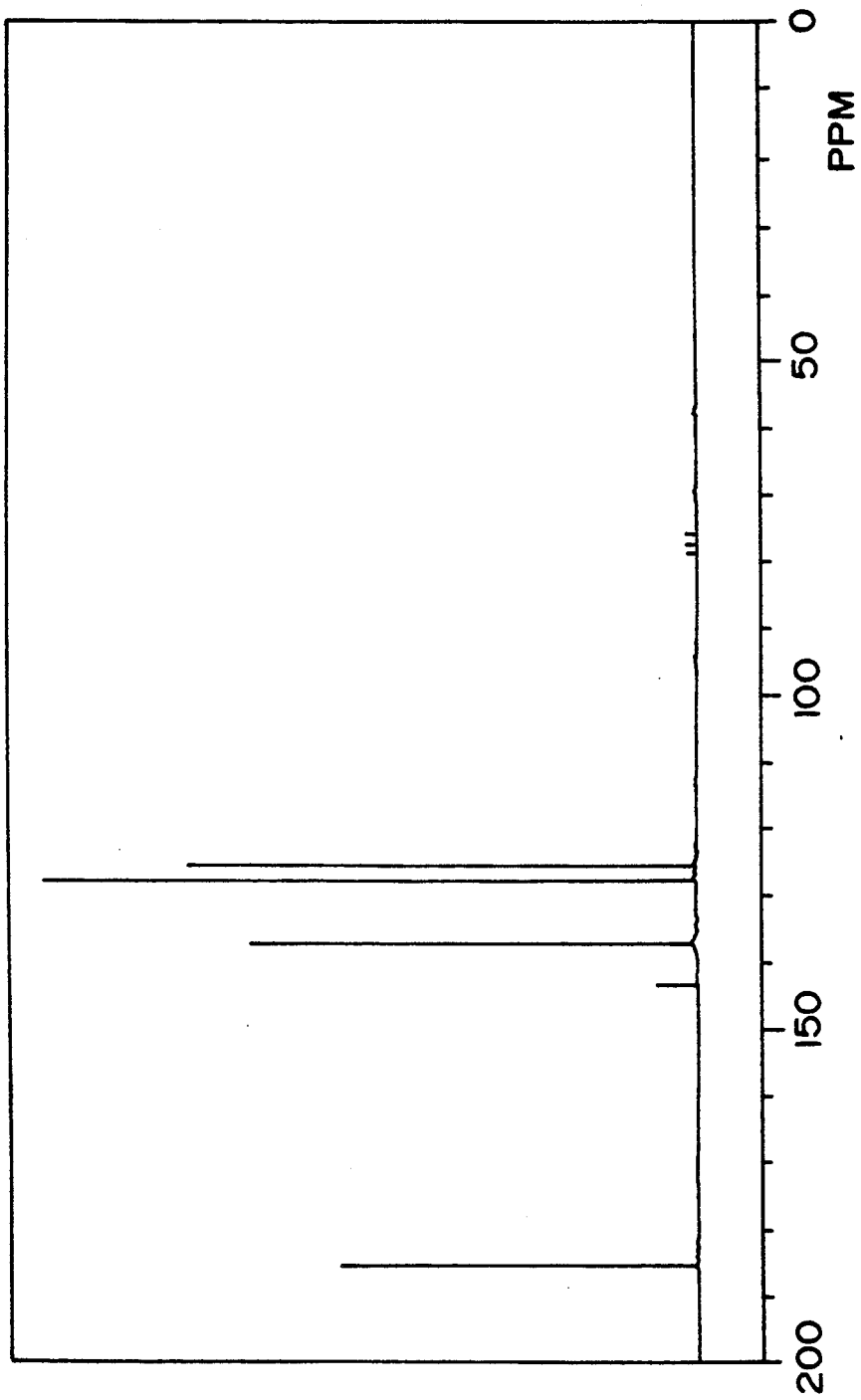
FIG. 1 is a $^{13}C$ nuclear magnetic resonance spectrum of 3-thiophene-carbaldehyde.

The photo-responsive material of the present invention comprises at least one of the thiophene derivatives having a long conjugated chain at the 3-position thereof, represented by the general formula (I) below.

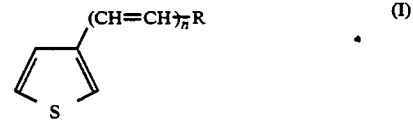
(I)

In the above formula (I), R is an aldehyde group, a carboxyl group, an alkyl ester group having linear alkyl of five carbons or less such as methyl carboxylate, ethyl carboxylate, and the like; an alkyl acetal group having linear alkyl of five carbon or less such as methyldioxane, methyldioxolane, and the like; and n is an integer of from 3 to 5, preferably 4 or 5.

The thiophene derivative of the present invention, having a long conjugated chain at the 3-position as represented by the above general formula (I) gives only one isomer on light irradiation, and the isomerization is reversible. Furthermore, the differences in wavelengths of absorption bands and in wavelengths of light-emission bands between the two isomers are great: the differences being confirmed to be not less than 100 nm in absorption band wavelengths and to be not less than 100 nm in emission band wavelengths depending on the compounds. Accordingly, the thiophene derivative of the present invention is suitable as a photo-responsive material such as an optical recording medium and an optical detecting material.

The methods for synthesis of the thiophene derivative having a long conjugated chain at the 3-position of the present invention are described below.

(1) According to the method of S. Trippet, et al. (J. Chem. Soc. 1266, 2130 (1961), 3-thiophene-carbaldehyde in which the 3-position of the thiophene ring is substituted by an aldehyde group is reacted with formylmethyltriphenylphosphorane to prepare a vinyl aldehyde having a double bond introduced between the 3-position of the thiophene ring and the aldehyde group. By repeating this reaction, an aldehyde derivative having a desired number of double bonds in the 3-position of a thiophene ring is prepared. From this thiophene derivative having an aldehyde group through a long conjugated chain at the 3-position, other compounds represented by the general formula (I) can be synthesized by reaction thereof with triphenylphosphorane having an alkyl ester group, or with triphenylphosphonium salt having an alkyl acetal group, and by further acid or alkali hydrolysis of the resulting compound having an alkyl ester group.

(2) According to the method of M. Terry, et al. (J. Chem. Soc., Perkin I, 37 (1974)), 3-thiophene-carbaldehyde in which the 3-position of the thiophene ring is substituted by an aldehyde group is reacted with 1,3-dioxolan-2-ylmethyltriphenylphosphonium bromide to prepare a vinyl acetal having a double bond introduced between the 3-position of the thiophene ring and the acetal group. The resulting compound is dissolved in organic solvent and reacted with aqueous hydrochloric acid solution to convert the acetal group into an aldehyde group. By repeating this reaction, an acetal derivative or an aldehyde derivative having a desired number of double bonds in the 3-position of the thiophene ring is prepared. From the aldehyde derivative, other compounds represented by the general formula (I) can be synthesized by reaction thereof with triphenylphosphorane having an alkyl ester group, and further acid or alkali hydrolysis of the resulting compound having an alkyl ester group.

(3) 2,4-hexadienedial is synthesized by the method of G. Kossmehl, et al. (Chem. Ber. 107, 710 (1974)). From this 2,4-hexadienedial is prepared a compound having two terminal aldehyde groups and even numbers of double bonds introduced according to the aforementioned method of M. Terry et al (J. Chem. Soc. Perkin I, 37 (1974)), and the resulting compound is reacted with 3-thienylmethyltriphenyl-phosphonium bromide to give an aldehyde derivative having an even number of double bonds introduced between the 3-position of the thiophene ring and the aldehyde group. From this thiophene derivative having an aldehyde group through a long conjugated chain at the 3-position, other compounds represented by the general formula (I) can be synthesized by reaction thereof with triphenyl-phosphorane having an alkyl ester group, or with triphenyl-phosphonium salt having an alkyl acetal group, and by further acid or alkali hydrolysis of the resulting compound having an alkyl ester group.

In this method, a polyene having a 3-substituted thiophene ring at both the ends respectively can be synthesized by varying the amount of 3-thienylmethyltriphenylphosphonium bromide.

The present invention is described specifically by reference to the following Examples.

EXAMPLE 1

5.6 g of 3-thiophenecarbaldehyde, which had been purified by distillation at a reduced pressure of 20 mmHg and at 86.7°–87.5° C., and 23.6 g of 1,3-dioxolan-2-ylmethyltriphenyl-phosphonium bromide synthesized by the method of M. Terry, et al. (J. Chem. Soc. Perkin I, 37 (1974)) were dissolved in 200 ml of DMF (dimethylformamide) having been dehydrated and purified with calcium hydride. Into this mixed solution kept at 75° C. to 86° C., a solution of 2.1 g of lithium methoxide in 80 ml of dehydrated methanol was added dropwise in 10 hours in a nitrogen atmosphere. After completion of the addition, the reaction mixture was cooled by standing to room temperature. Then 500 ml of water was added thereto, and the mixture was extracted with 400 ml of diethyl ether three times. The diethyl ether solution was dried over anhydrous magnesium sulfate. This solution was concentrated, and thereto a mixed solvent of hexane-ethyl acetate (9:1) was added. Triphenylphosphine oxide formed was separated by filtration. To the filtrate, tetrahydrofuran (THF) was added to a total volume of 200 ml. Thereto 150 ml of aqueous 10% hydrochloric acid solution was added and the mixture was stirred for 3 hours. After removal of the THF, 100 ml of water was added to the solution, and the mixture was extracted with 300 ml of diethyl ether three times. The diethyl ether solution was neutralized with aqueous sodium hydrogen carbonate solution, and dried over anhydrous magnesium sulfate. The diethyl ether was removed, and the residue was vacuum-distilled under pressure of 0.5 mmHg to give 4.5 g (Yield: 65%) of a pale green liquid at 90°–92° C.

Figure 2:
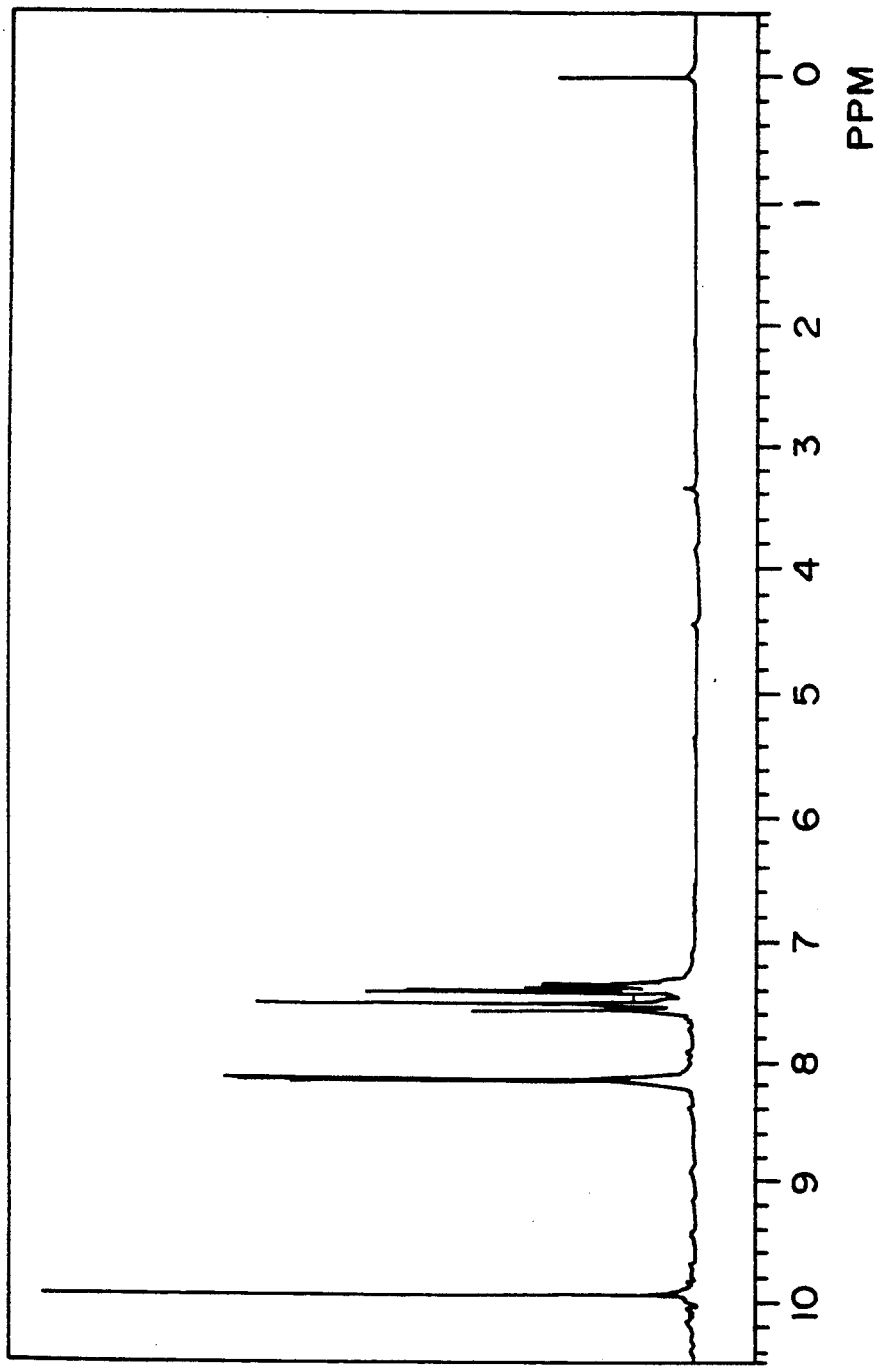
FIG. 2 is a $^{1}H$ nuclear magnetic resonance spectrum of 3-thiophene-carbaldehyde.
Figure 3:
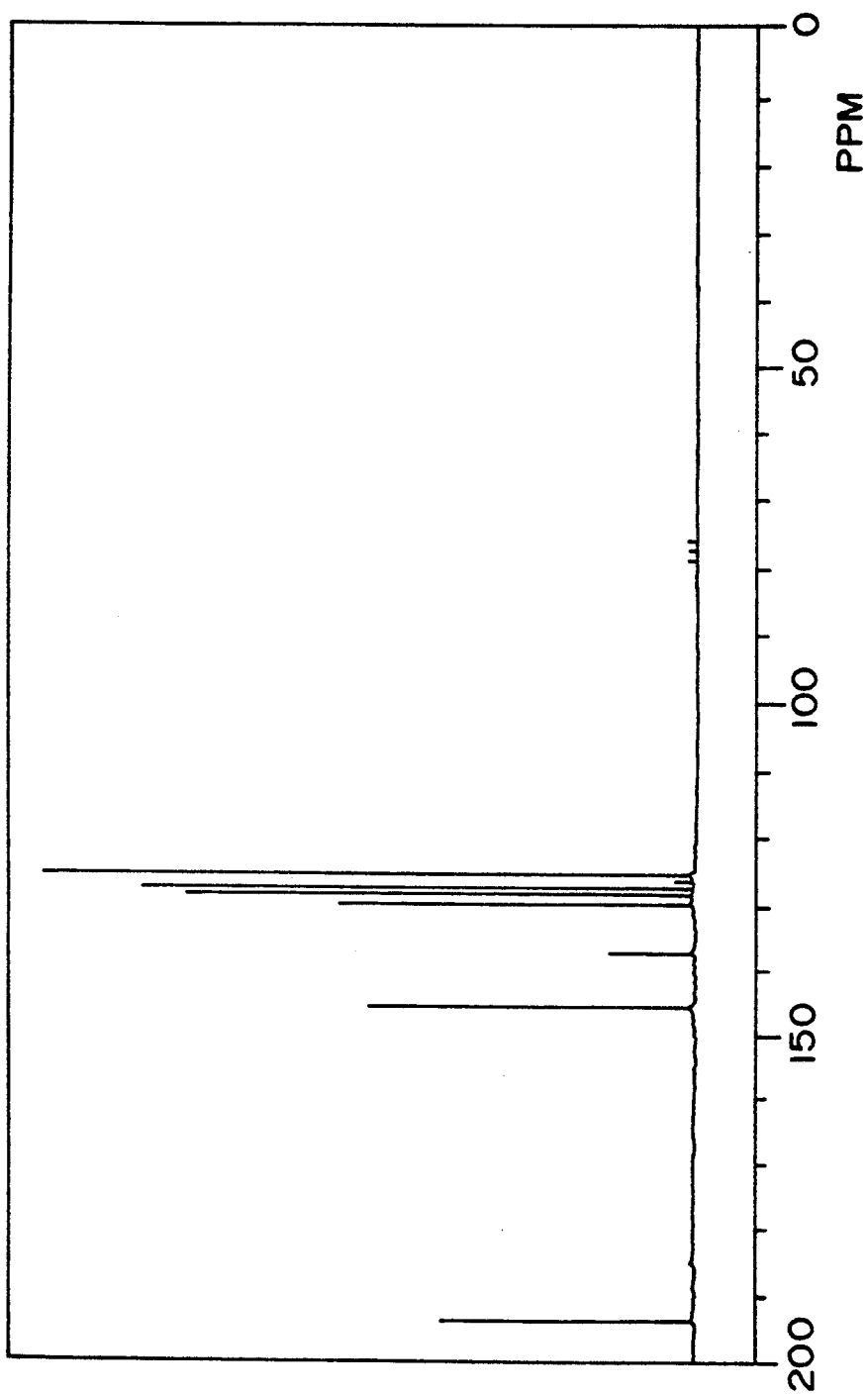
FIG. 3 is a $^{13}C$ nuclear magnetic resonance spectrum of 3-(3-thienyl)-2-propenal.
Figure 4:
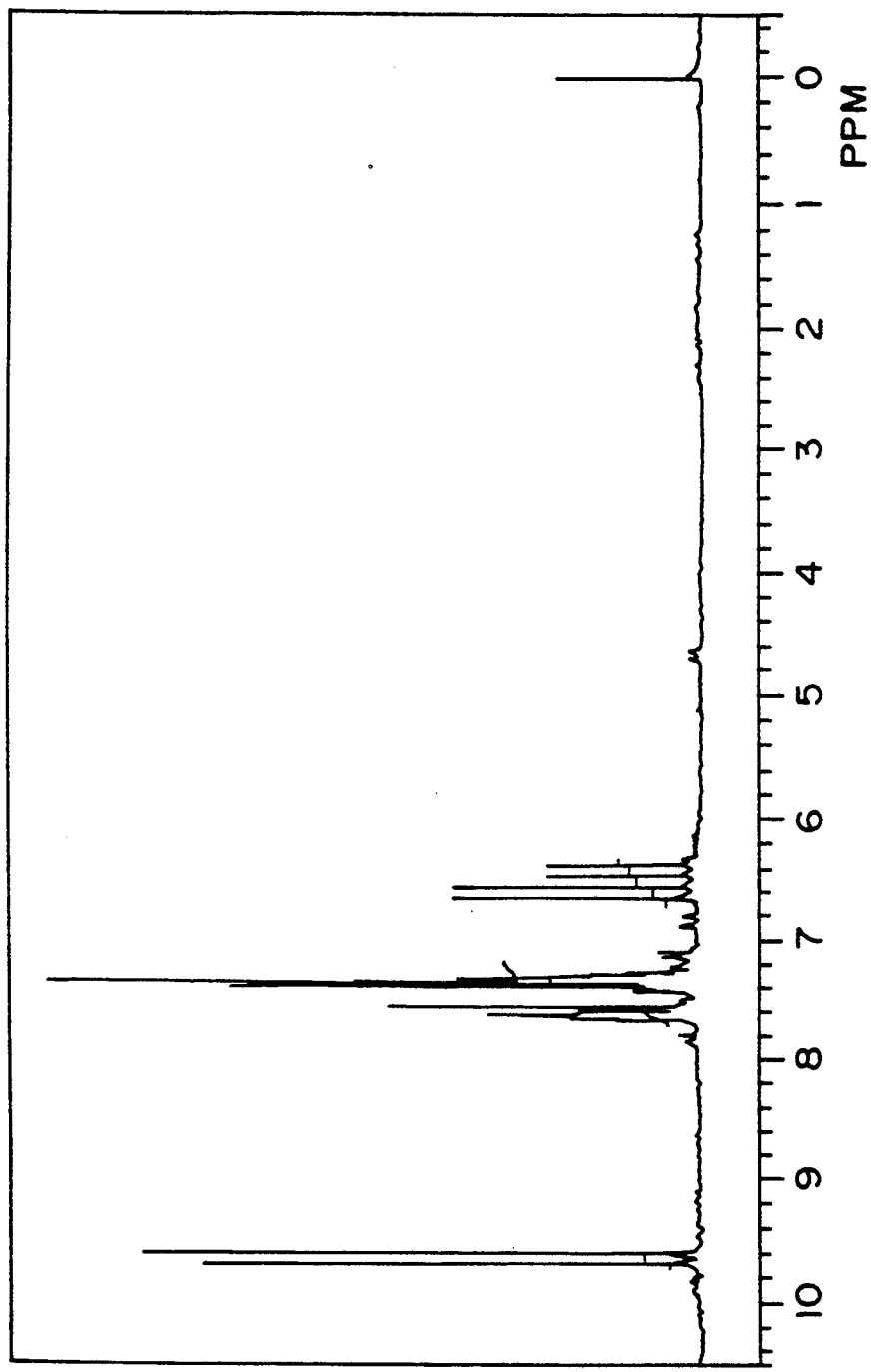
FIG. 4 is a $^{1}H$ nuclear magnetic resonance spectrum of 3-(3-thienyl)-2-propenal.

The $^{13}C$ nuclear magnetic resonance spectrum (FIG. 3) of this pale green liquid shows seven carbons, namely five carbons (125.2, 127.4, 136.8, 143.0, and 184.9 ppm) of 3-thiophene-carbaldehyde (FIG. 1) and additionally two carbons (128.2, and 129.6 ppm). Further, the $^1H$ nuclear magnetic resonance spectrum (FIG. 4) shows two double-bond hydrogens, in addition to those of 3-thiophenecarbaldehyde (FIG. 2).

Further, from the elemental analysis of this compound, C:H:O:S=7:6:1:1 (C=60.76%, H=4.45%, O=11.59%, S=23.20%). Accordingly, this pale green liquid was identified as 3-(3-thienyl)-2-propenal which has a double bond between the aldehyde group and the 3-position of the thiophene ring.

Figure 5:
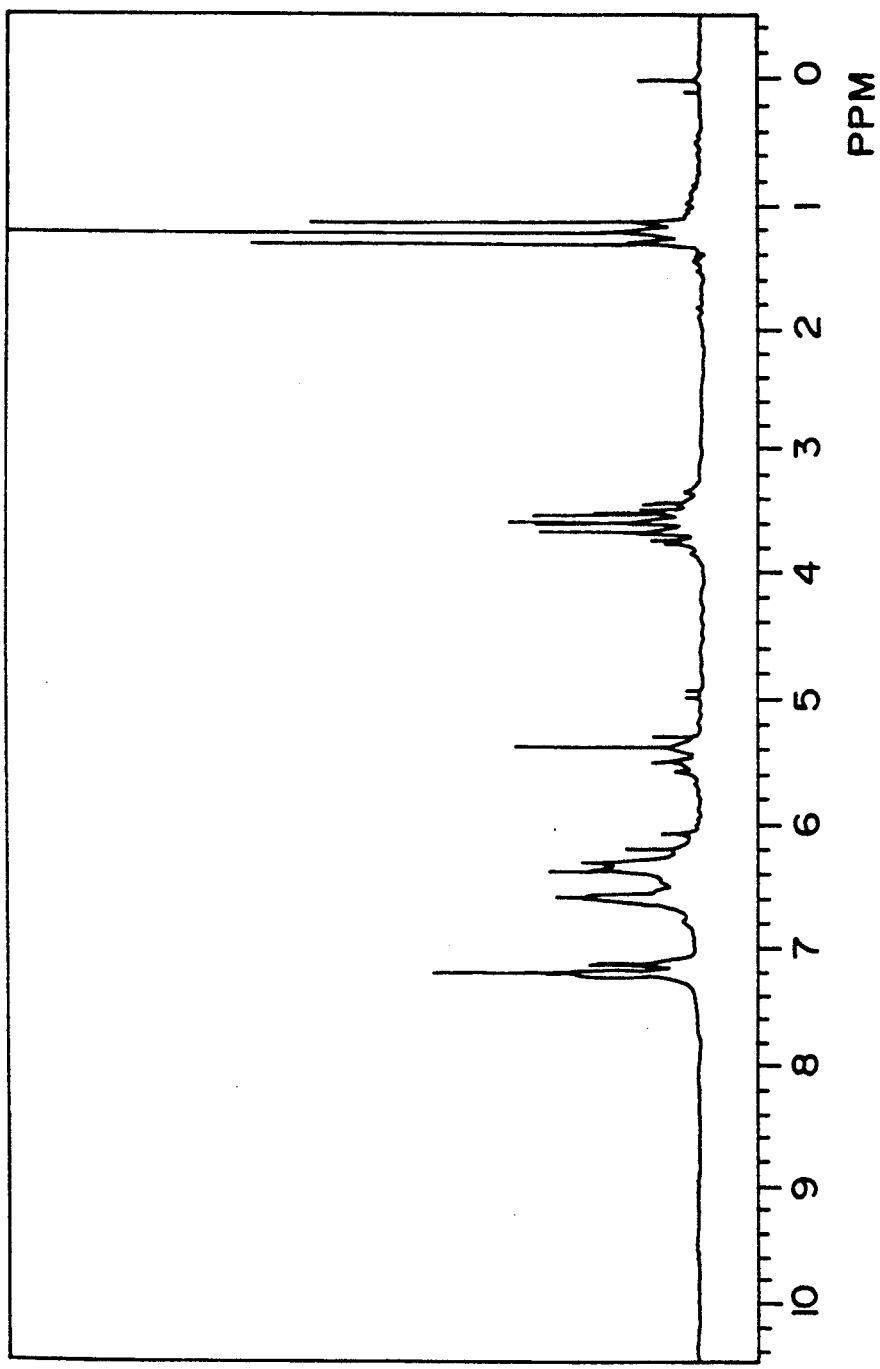
FIG. 5 is a $^{1}H$ nuclear magnetic resonance spectrum of 11-(3-thienyl)-1,3-dioxolan-2-ylocta-4,6,8,10-tetraene.
Figure 6:
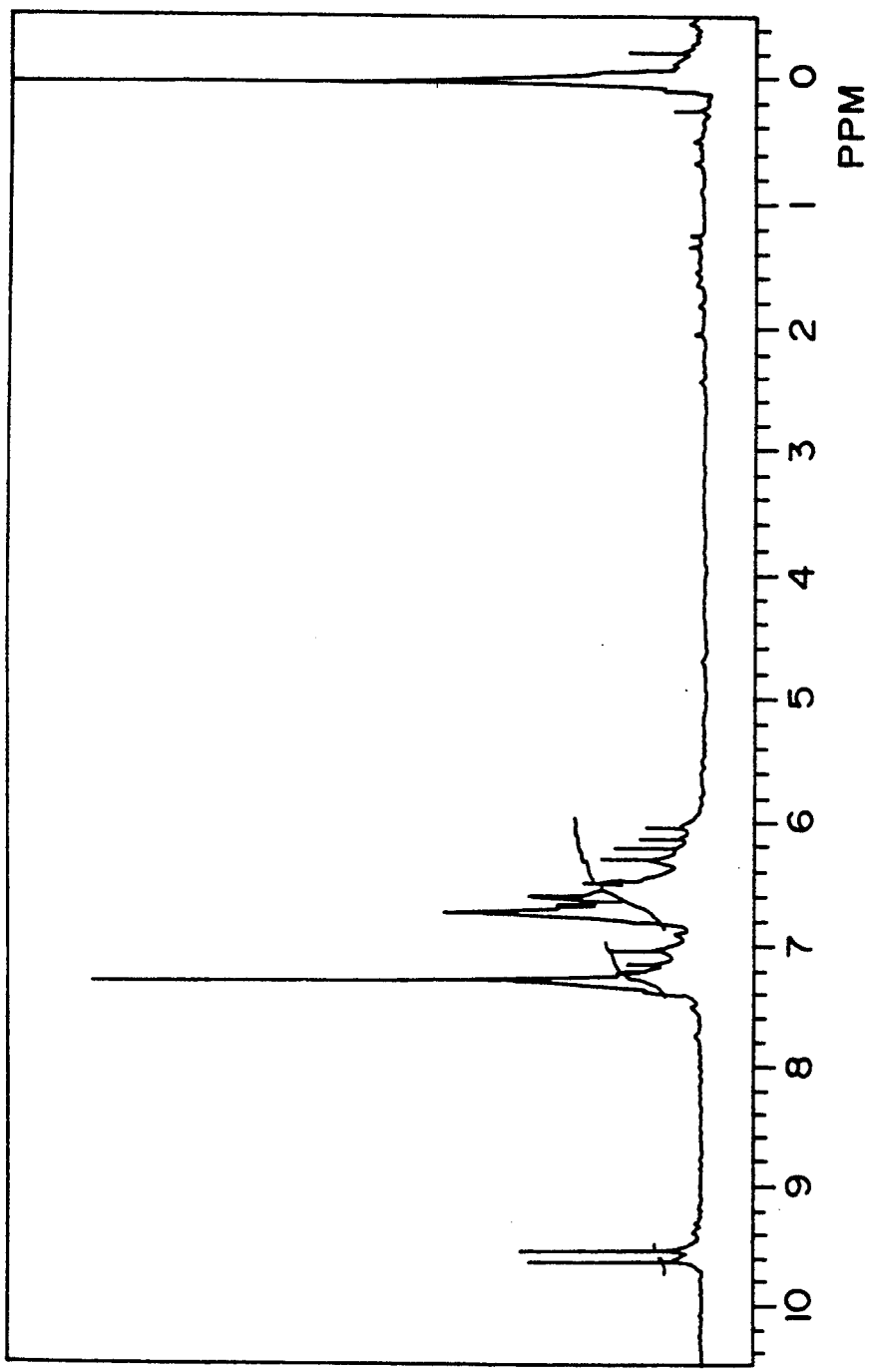
FIG. 6 is a $^{1}H$ nuclear magnetic resonance spectrum of 9-(3-thienyl)nona-2,4,6,8-tetraenal.

The above procedure was further repeated three times, giving 11-(3-thienyl)-1,3-dioxolan-2-ylocta-4,6,8,10-tetraene which has four double bonds between the acetal group and the 3-position of the thiophene ring. Hydrolysis of this compound gave 9-(3-thienyl)-nona-2,4,6,8-tetraenal. Both the compounds were identified by $^1H$ nuclear magnetic resonance spectrum, $^{13}C$ nuclear magnetic resonance spectrum, and elemental analysis. FIG. 5 shows the $^1H$ nuclear magnetic resonance spectrum of 11-(3-thienyl)-1,3-dioxolan-2-ylocta-4,6,8,10-tetraene. FIG. 6 shows the $^1H$ nuclear magnetic resonance spectrum of 9-(3-thienyl)nona-2,4,6,8-tetraenal. The 9-(3-thienyl)nona-2,4,6,8-tetraenal was found to have a melting point of 156°–158° C.

0.45 g of the 9-(3-thienyl)nona-2,4,6,8-tetraenal and 0.9 g of methyl (triphenylphosphoranylidene)acetate (made by Aldrich Co.) were dissolved in 100 ml of dehydrated and purified benzene. The solution was refluxed for four days in nitrogen atmosphere, treated with active carbon, and was left standing for cooling. Thereby yellow needle crystalline matter deposited.

Figure 7:
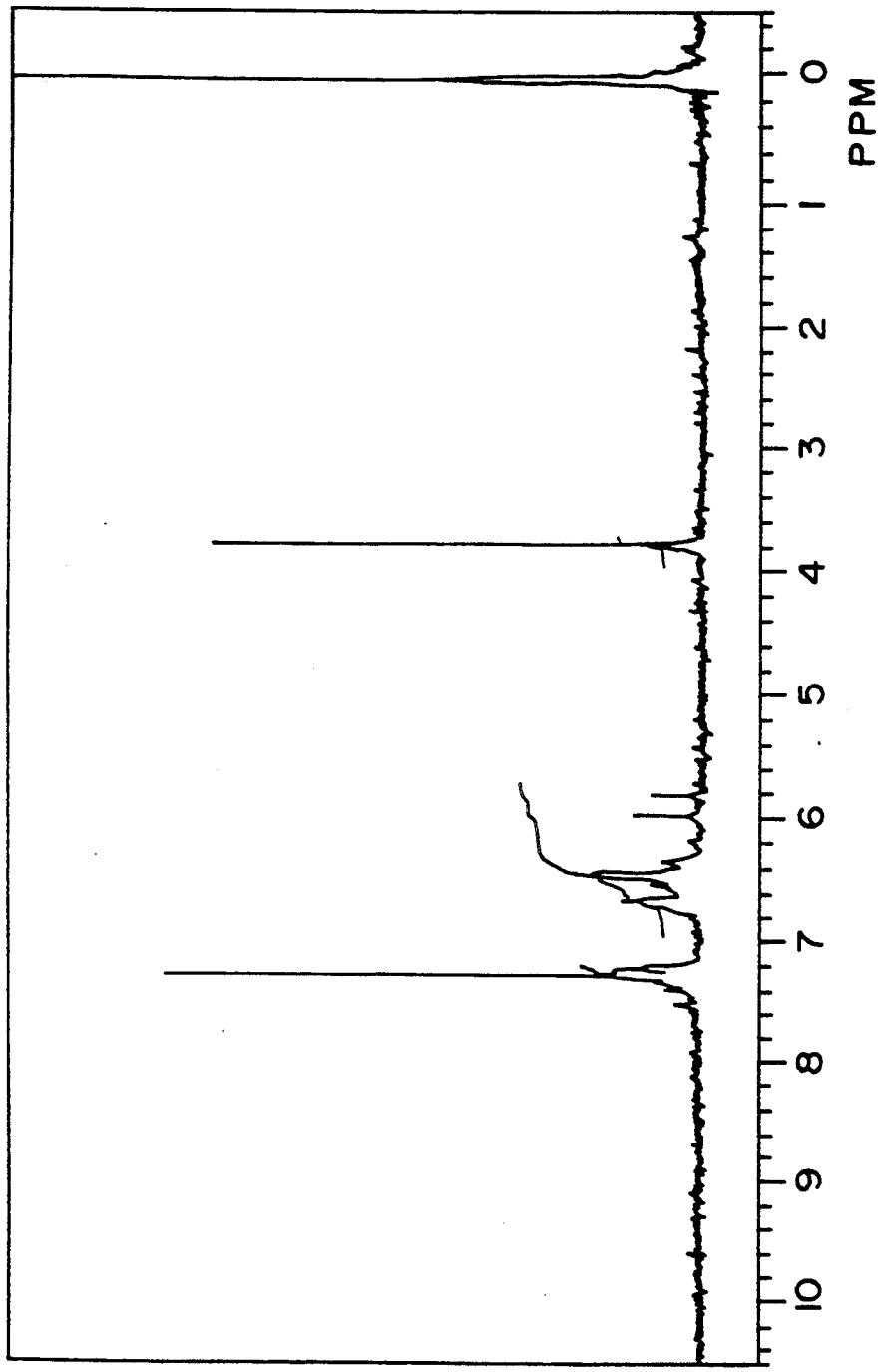
FIG. 7 is a $^{1}H$ nuclear magnetic resonance spectrum of methyl 11-(3-thienyl)undeca-2,4,6,8,10-pentaene-carboxylate.
Figure 8:
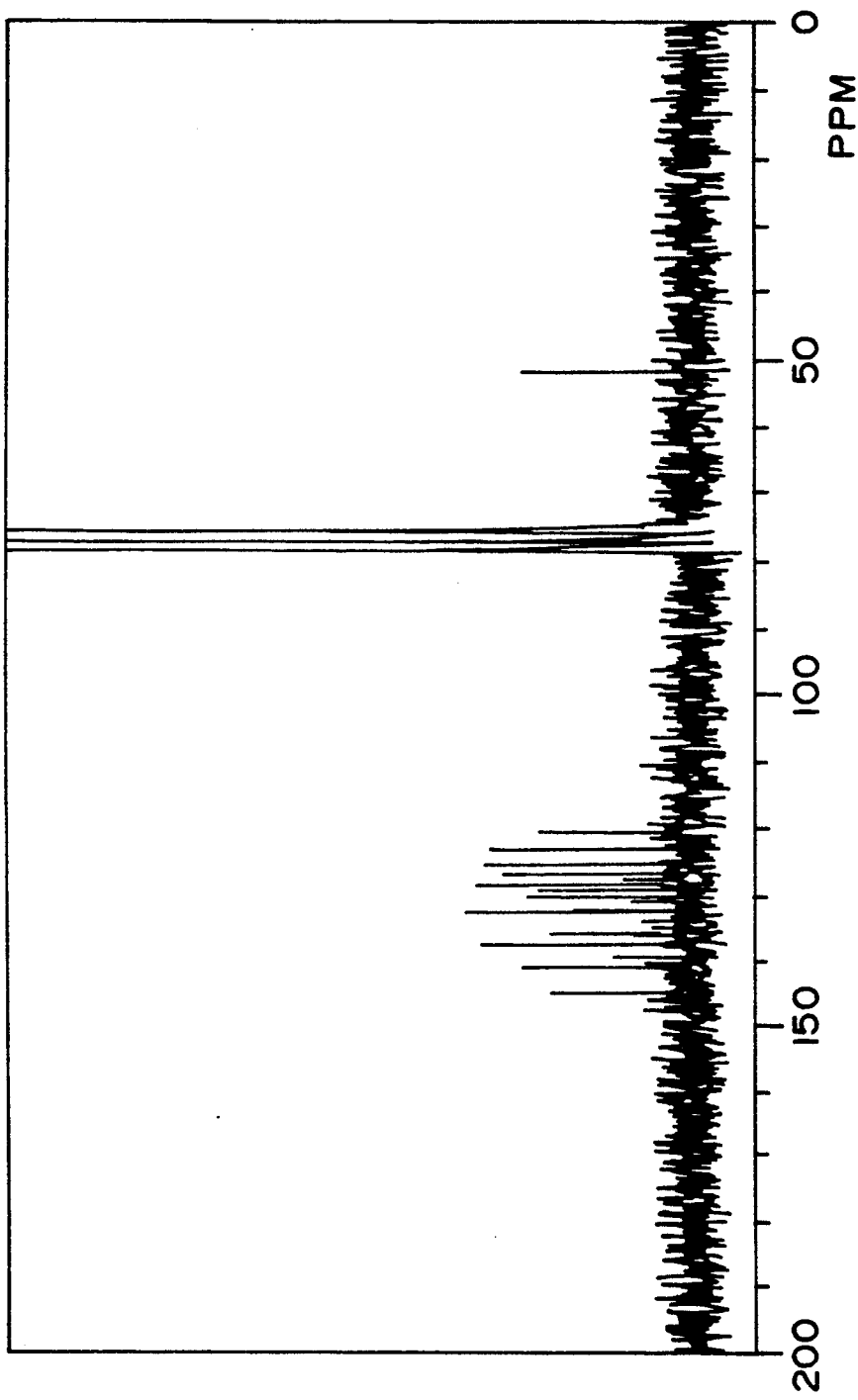
FIG. 8 is a $^{13}C$ nuclear magnetic resonance spectrum of methyl 11-(3-thienyl)undeca-2,4,6,8,10-pentaene-carboxylate.

This crystalline matter was collected by filtration and vacuum dried, giving 0.25 g (yield: 49%) of methyl 11-(3-thienyl)undeca-2,4,6,8,10-pentaene-carboxylate. This compound was identified by $^1$H nuclear magnetic resonance spectrum (FIG. 7), $^{13}$C nuclear magnetic resonance spectrum (FIG. 8), and elemental analysis (C=70.49%, H=5.82%, O=11.89%, S=11.80%, C:H:O:S=16:16:2:1). The melting point was 206°–208° C.

0.05 g of the methyl 11-(3-thienyl)undeca-2,4,6,8,10-pentaene-carboxylate prepared as above was dissolved 100 ml of a mixed solvent of THF-ethanol (1:1). The solution was stirred with 0.08 g of potassium hydroxide and 10 ml of water at room temperature for 5 days. Thereafter aqueous sulfuric acid solution was added to the above solution to give pH 4, thereby forming a yellow precipitate. The yellow precipitate was washed twice with water and twice with ethanol and vacuum-dried, giving 0.014 g of yellow powder. This compound was hardly soluble in organic solvents and water, but slightly soluble in DMSO (dimethylsulfoxide), DMF, and acetone. The $^1$H nuclear magnetic resonance thereof in deuterium-substituted DMSO showed peaks closely resembling those of the starting methyl 11-(3-thienyl)undeca-2,4,6,8,10-pentaene-carboxylate at 5.6–7.6 ppm. From the disappearance of the peak of a methyl ester at 3.6 ppm, and the peak number of 15 in $^{13}$C nuclear magnetic resonance spectrum, this yellow powder was identified as 11-(3-thienyl)undeca-2,4,6,8,10-pentaene-carboxylic acid which is a hydrolysis product of methyl 11-(3-thienyl)undeca-2,4,6,8,10-pentaene-carboxylate. This compound changed its color from yellow to orange at about 160° C., and further to yellow at about 230° C., and decomposed at 250° C. or higher to become black.

EXAMPLE 2

2,4-hexadienedial was synthesized according to the method of G.Kossmehl, et al. (Chem. Ber. 107, 710 (1974)). 1,3-dioxolan-2-ylmethyltriphenylphosphonium bromide was synthesized according to M. Terry, et al. (J. Chem. Soc., Perkin I, 37 (1974). 1.1 g of the 2,4-hexadienedial and 2.3 g of the 1,3-dioxolan-2-ylmethyltriphenylphosphonium bromide were added to 100 ml of dehydrated and purified DMF. Thereto, 0.2 g of lithium methoxide dissolved in 20 ml of dehydrated methanol was added dropwise at temperature of 75° to 85° C. in 5 hours. This reaction solution was left standing to be cooled to room temperature. 500 ml of water was added to the reaction solution, and the mixture was extracted with diethyl ether. The diethyl ether was removed from the extract with an evaporator. The evaporation residue was introduced to an alumina column (neutral, activity I), and eluted with a mixed solvent of hexane-ethyl acetate (9:1). The solvent was removed with an evaporator. The evaporation residue was vacuum-dried to give 0.85 g of pale yellow powder. 0.85 g of this pale yellow powder and 2.1 g of 3-thienylmethyltriphenylphosphonium bromide synthesized by the method of W. J. Archer, et al. (J.C.S., Perkin Trans. II, 813 (1983) were added to 60 ml of dehydrated and purified DMF. Thereto, 0.2 g of lithium methoxide dissolved in 20 ml of dehydrated methanol was added at temperature of 75° to 85° C. in 5 hours. This reaction solution was extracted and purified in the same manner as described above. The resulting yellow powder was treated with active carbon, and recrystallized, to give 0.47 g of yellow crystalline powder. The $^1$H nuclear magnetic resonance spectrum of this power coincided with the one shown in FIG. 5, end was identified as 11-(3-thienyl)-1,3-dioxolan-2-ylocta-4,6,8,10-tetraene.

EXAMPLE 3

10 g of formylmethyltriphenylphosphorane synthesized by the method of S. Trippett, et al. (J. Chem. Soc., 1266 (1961)) and 3.6 g of 3-thiophenecarbaldehyde purified in the same manner as in Example 1 were dissolved in 600 ml of benzene having been dehydrated and purified with sodium. The solution was refluxed in nitrogen atmosphere. After confirmation of the reaction of the formylmethyltriphenyl-phosphorane by thin-layer chromatography, further 10 g of formylmethyltriphenylphosphorane was added. This procedure was repeated once more. After confirmation of the completion of the reaction of formylmethyl-triphenylphosphorane by thin-layer chromatography, the reaction solution was cooled to room temperature by standing, and then concentrated. Thereto a mixed solution of hexaneethyl acetate (9:1) was added to precipitate triphenylphosphine oxide, which was eliminated by filtration. The filtrate was concentrated. The concentrated matter was separated and purified by use of an alumina column, giving 0.76 g of yellow crystalline substance.

Figure 9:
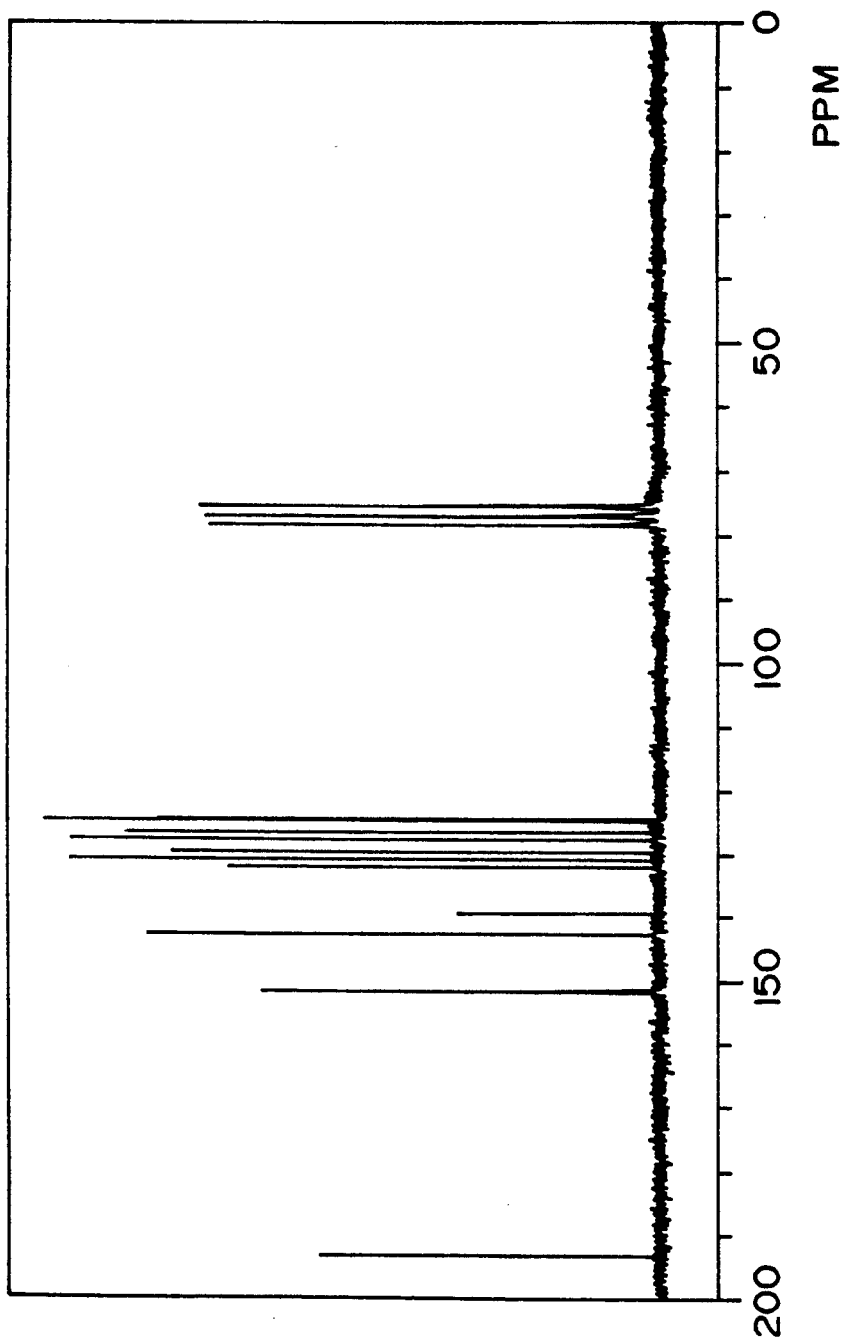
FIG. 9 is a $^{13}C$ nuclear magnetic resonance spectrum of 7-(3-thienyl)hepta-2,4,6-trienal.
Figure 10:
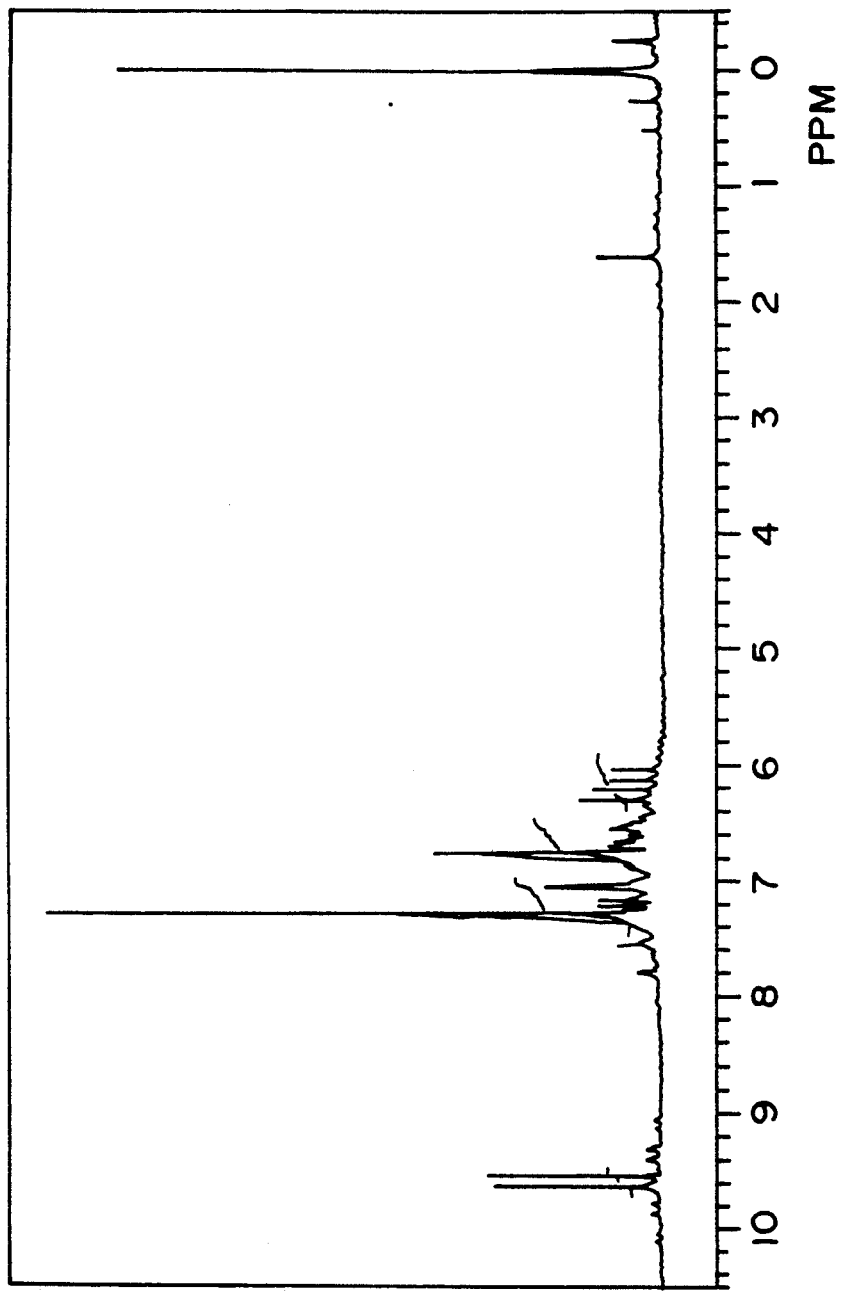
FIG. 10 is a $^{1}H$ nuclear magnetic resonance spectrum of 7-(3-thienyl)hepta-2,4,6-trienal.

The crystalline substance gave the $^{13}$C nuclear magnetic resonance spectrum as shown in FIG. 9, corresponding to 11 carbons of 3-thiophenecarbaldehyde (5 carbons, shown in FIG. 3) and 6 double-bonded carbons added thereto. The substance also gave $^1$H nuclear magnetic resonance spectrum as shown in FIG. 10, corresponding to 3-thiophenecarbaldehyde (FIG. 2) and 6 hydrogen atoms of double bonds.

The elemental analysis of the substance gave the values of C:H:O:S=11:10:1:1 (C=69.14%, H=5.50%, O=8.51%, and S=16.75%). Consequently the substance was identified as 7-(3-thienyl)hepta-2,4,6-trienal having three double bonds between the aldehyde group and the 3-position of the thiophene ring of 3-thiophenecarbaldehyde.

EXAMPLE 4

A $4.7 \times 10^{-6}$ mol/Q solution in chloroform of methyl 11-(3-thienyl)undeca-2,4,6,8,10-pentaenecarboxylate prepared in Example 1 was irradiated by light of a xenon lamp. Thereby the absorption spectrum of the solution changed, as shown in FIG. 11, from a spectrum (a) having the absorption maximum at 392 nm to a spectrum (b) having the absorption maximum at 278 nm with the change of absorption band by 100 nm or more, the solution turning colorless from yellow.

This change was reversible. When the compound giving the spectrum (b) of FIG. 11 was irradiated by light of wavelength of 600 nm or more, the spectrum changed to the spectrum (a). The element composition ratio of the compound giving the spectrum (b) was found to be C:H:O:S=16:16:2:1 according to elemental analysis. Thereby, the compound giving the spectrum (b) was identified as an isomer of methyl 11-(3-thienyl)undeca- 2,4,6,8,10-pentaenecarboxylate.

Figure 11:
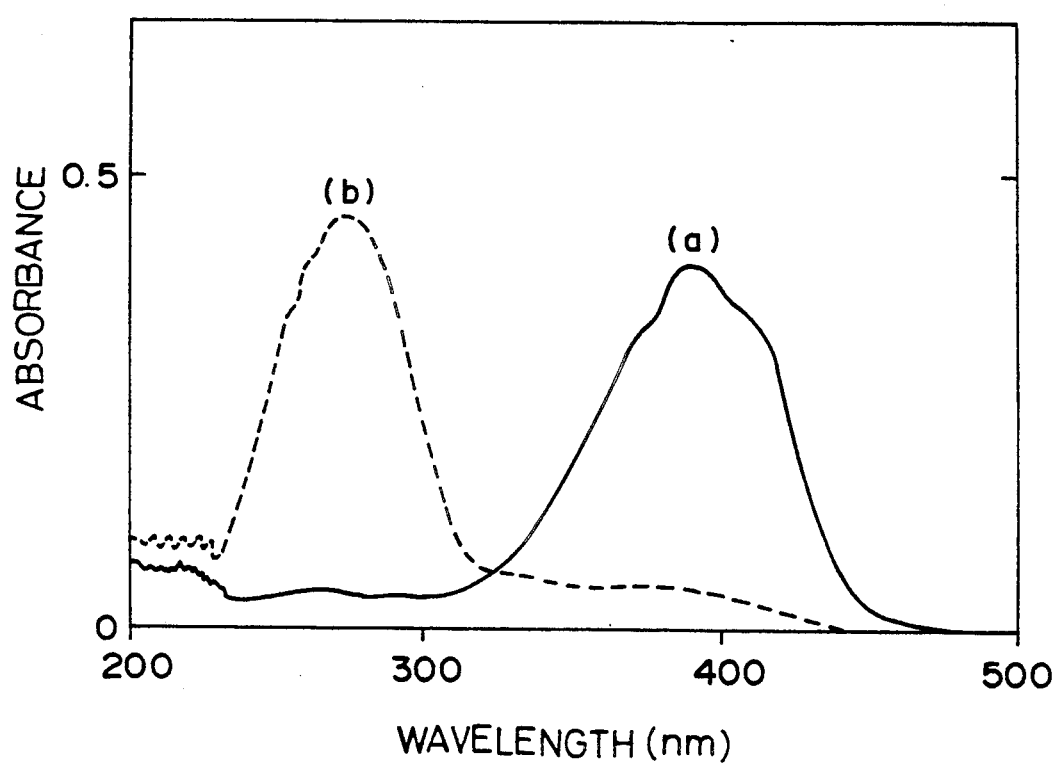
FIG. 11 shows the absorption spectrum (a) of methyl 11-(3-thienyl)undeca-2,4,6,8,10-pentaene-carboxylate, and the absorption spectrum (b) thereof after light irradiation.

In light emission spectrum measurement of both the compounds, the methyl 11-(3-thienyl)undeca-2,4,6,8,10-pentaenecarboxylate having the spectrum (a) of FIG. 11 gave an emission spectrum having a maximum at around 560 nm by expiration light of 390 nm, while the isomer having the spectrum (b) of FIG. 11 gave an emission spectrum having a maximum at around 440 nm by excitation light of 290 nm. Thus the differences of 100 nm in excitation light and 120 nm in emission band were observed between the isomers.

EXAMPLES 5 AND 6

The compounds prepared in Example 2 and Example 3 will change respectively to the corresponding isomers on light irradiation in approximately the same manner as in Example 4.

As described above, the thiophene derivative having a long conjugated chain at the 3-position represented by the aforementioned general formula (I) has characteristics below:

(1) The thiophene derivative gives only one isomer on light irradiation.

(2) The wavelength difference of the absorption band and the wavelength change of the emission band are large, allowing ready discrimination of the isomers. and (3) The conversion between the isomers is reversible.

Accordingly the thiophene derivative of the present invention provides a photo-responsive material which is useful as optical recording medium and optical detection material.

What is claimed is:

1. A photo-responsive material, containing a thiophene derivative having a long conjugated chain at the 3-position thereof represented by the general formula (I):

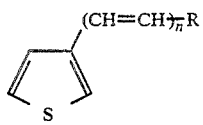

where R is a group selected from an aldehyde group, a carboxyl group, an alkyl ester group, and an alkyl acetal group, and n is an integer of from 3 to 5; wherein an original isomer of said thiophene derivative is capable of reversibly changing to only one other isomer having light-absorption bands and light-emission bands different from those of the original isomer.

2. The photo-responsive material of claim 1, wherein the integer n is 4.

3. The photo-responsive material of claim 1, wherein the integer n is 5.

4. The photo-responsive material of claim 1, wherein R is methyl carboxylate or ethyl carboxylate.

5. The photo-responsive material of claim 1, wherein R is methyldioxane or methyldioxolane.

6. The photo-responsive material of claim 1, wherein the compound of the general formula (I) is 11-(3-thienyl)-undeca-2,4,6,8,10-pentaenecarboxylic acid.

7. The photo-responsive material of claim 1, wherein the compound of the general formula (I) is 11-(3-thienyl)-1,3-dioxolan-2-ylocta-4,6,8,10-tetraene.

8. The photo-responsive material of claim 1, wherein the compound of the general formula (I) is 7-(3-thienyl)-hepta-2,4,6-trienal.

9. A method for isomerizing comprising light-irradiation of a photo-responsive material comprising a thiophene derivative having a long conjugated chain at the 3-position thereof represented by the general formula (I):

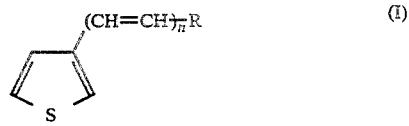

where R is selected from an aldehyde group, a carboxyl group, an alkyl ester group, and an alkyl acetal group, and n is an integer of from 3 to 5.

10. The method of claim 9, wherein a solution of the thiophene derivative of the general formula (I) is irradiated by light.

11. The method of claim 9, wherein the integer n is 4.

12. The method of claim 9, wherein the integer n is 5.

13. The method of claim 9, wherein R is methyl carboxylate or ethyl carboxylate.

14. The method of claim 9, wherein R is methyldioxane or methyldioxolane.

15. The method of claim 9, wherein the compound of the general formula (I) is 11-(3-thienyl)-undeca-2,4,6,8,10-pentaenecarboxylic acid.

16. The method of claim 9, wherein the compound of the general formula (I) is 11-(3-thienyl)-1,3-dioxolan-2-ylocta- 4,6,8,10-tetraene.

17. The method of claim 9, wherein the compound of general formula (I) is 7-(3-thienyl)-hepta-2,4,6-trienal.

* * * * *